United States Patent
Arif et al.

(10) Patent No.: US 9,501,950 B2
(45) Date of Patent: Nov. 22, 2016

(54) SYSTEM AND METHOD FOR COACH DECISION SUPPORT

(71) Applicant: UMM AL-QURA UNIVERSITY, Makkah (SA)

(72) Inventors: Muhammad Arif, Makkah (SA); Ahmed Kattan, Makkah (SA)

(73) Assignee: Umm Al-Qura University, Makkah (SA)

( * ) Notice: Subject to any disclaimer, the term of this patent is extended or adjusted under 35 U.S.C. 154(b) by 62 days.

(21) Appl. No.: 14/400,862

(22) PCT Filed: Nov. 7, 2014

(86) PCT No.: PCT/IB2014/002390
§ 371 (c)(1),
(2) Date: Nov. 13, 2014

(87) PCT Pub. No.: WO2016/071726
PCT Pub. Date: May 12, 2016

(65) Prior Publication Data
US 2016/0133152 A1    May 12, 2016

(51) Int. Cl.
| | |
|---|---|
| *A63F 13/06* | (2006.01) |
| *G09B 19/00* | (2006.01) |
| *A63B 24/00* | (2006.01) |
| *G06Q 99/00* | (2006.01) |
| *G09B 5/00* | (2006.01) |

(52) U.S. Cl.
CPC ....... *G09B 19/0038* (2013.01); *A63B 24/0062* (2013.01); *G06Q 99/00* (2013.01); *G09B 5/00* (2013.01)

(58) Field of Classification Search
CPC .................. A63F 13/12; A63F 2300/1025
See application file for complete search history.

(56) References Cited

U.S. PATENT DOCUMENTS

| 5,354,050 A | 10/1994 | McCarthy et al. |
|---|---|---|
| 6,331,168 B1 | 12/2001 | Socci et al. |

(Continued)

FOREIGN PATENT DOCUMENTS

| EP | 1 992 389 A1 | 11/2008 |
|---|---|---|
| WO | WO 01/66006 A1 | 9/2001 |

(Continued)

OTHER PUBLICATIONS

Hiskett, P. A., et al. "Kinexon ONE is a precision athlete monitoring system", http://sport.kinexon.com, (9 Pages), 2000.

(Continued)

*Primary Examiner* — Omkar Deodhar
(74) *Attorney, Agent, or Firm* — Oblon, McClelland, Maier & Neustadt, L.L.P.

(57) ABSTRACT

A coach decision support method including collecting sensor data associated with an athlete at a data logger circuitry; wherein sensor data is generated by at least one sensor placed on the athlete; pre-processing the sensor data at the data logger circuitry and filtering sensor noise from the collected sensor data; extracting at least one feature of the collected sensor data; classifying the at least one extracted feature into at least one physical activity; transmitting the physical activity classification to a data analysis module; generating a detailed report of the physical activity analyzing the athlete's performance within a sporting arena; and generating at least one coach decision recommendation based at least in part on the generated detailed report.

19 Claims, 14 Drawing Sheets

(56) References Cited

U.S. PATENT DOCUMENTS

| | | | |
|---|---|---|---|
| 8,672,810 B2 | 3/2014 | Molyneux et al. | |
| 2003/0181832 A1 | 9/2003 | Carnahan et al. | |
| 2005/0021292 A1* | 1/2005 | Vock | A42B 3/0433 702/182 |
| 2006/0136173 A1* | 6/2006 | Case, Jr. | A63B 24/00 702/182 |
| 2007/0066415 A1 | 3/2007 | Hou et al. | |
| 2007/0219059 A1 | 9/2007 | Schwartz et al. | |
| 2008/0284650 A1 | 11/2008 | MacIntosh et al. | |
| 2012/0116550 A1 | 5/2012 | Hoffman et al. | |
| 2013/0110011 A1 | 5/2013 | McGregor et al. | |
| 2013/0128022 A1* | 5/2013 | Bose | H04N 7/18 348/77 |
| 2013/0173033 A1 | 7/2013 | Oleson et al. | |
| 2013/0274635 A1 | 10/2013 | Coza et al. | |
| 2014/0031703 A1 | 1/2014 | Rayner et al. | |
| 2014/0228988 A1 | 8/2014 | Hoffman et al. | |

FOREIGN PATENT DOCUMENTS

| | | |
|---|---|---|
| WO | WO 2012/021507 A2 | 2/2012 |
| WO | WO 2012/021507 A3 | 2/2012 |
| WO | WO 2014/022438 A1 | 2/2014 |

OTHER PUBLICATIONS

International Search Report and Written Opinion issued Jul. 7, 2015 in PCT/IB2014/002390.

* cited by examiner

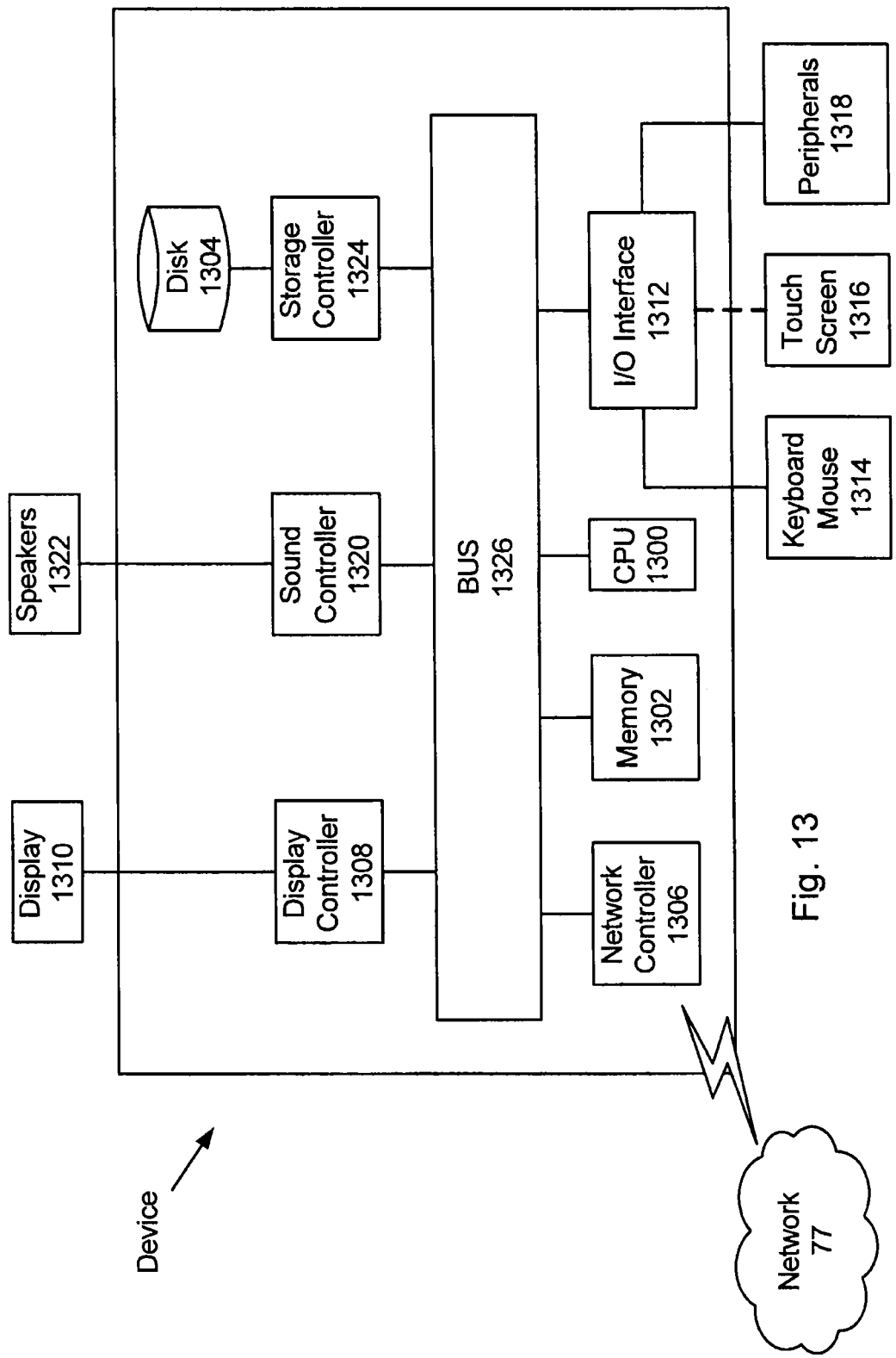

SYSTEM AND METHOD FOR COACH DECISION SUPPORT

BACKGROUND

Description of the Related Art

The present disclosure relates generally to systems and method for intelligently monitoring athlete activities on the field and recommend actions based on monitored activities.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Athletic activity is important to maintain a healthy lifestyle and is a source of entertainment for many people. Some individuals prefer to engage in team athletic activities, such as, for example, soccer or basketball, while other individuals prefer to engage in individual athletic activities, such as, for example, running or playing tennis. Regardless of the activity, it is common for individuals to participate in both competitive sessions, such as a soccer match or running race, and more informal training sessions such as conducting soccer drills or running interval sprints.

Monitoring activity profile of players during sports activities is studied by many researchers. This kind of monitoring enables sports scientists and coaches to devise new training programs. This monitoring includes heart rate, total time of different activities of running, walking, sprinting, jogging, jumping and standing etc. Muscle activities are also important in the monitoring of players activities. In case of soccer game, there may be additional activities like tackling the opponent players, kicking of ball etc. For activity monitoring, different researchers have used recording and analysis of videos during the regular matches. Research work has been focused on proper arrangement of cameras on the ground to capture the movements of every player in the ground.

What is needed are new athletic activity monitoring methods and systems to have advanced capabilities that monitor the performance of athletes and provide summaries, analysis and coaching decision aid solutions.

SUMMARY

In one embodiment, there may be a coach decision support method including collecting sensor data associated with an athlete at a data logger circuitry, wherein the sensor data is generated by at least one sensor placed on the athlete, pre-processing the sensor data at the data logger circuitry by filtering sensor noise from the sensor data, extracting at least one feature set from the collected sensor data, classifying with the circuitry the at least one extracted feature set into at least one physical activity, transmitting the physical activity classification to a data analysis circuitry, generating with the data analysis circuitry a report of the physical activity indicative of a performance of the athlete within a sporting arena, and generating with the data analysis circuitry at least one coach decision recommendation based at least in part on the report.

The method may further include collecting global positioning (GPS) data associated with a position of the athlete, generating a player localization map, and transmitting the player localization map to the data analysis module. Wherein the extracting further includes extracting a heart rate associated with the athlete, and generating an energy expenditure associated with the athlete. And wherein the generating the energy expenditure further includes collecting temperature and humidity data, identifying the physical activity for a predetermined time window, and calculating with the data analysis circuitry the energy expenditure by the physical activity as a function of the physical activity and the predetermined time window. The method further includes calculating with the data analysis circuitry a heat index as a function of temperature and humidity, modifying the energy expenditure by the heat index, and calculating with the data analysis circuitry a total modified energy expenditure of the athlete.

The pre-processing sensor data further includes filtering noise associated with at least one sensor to minimize interference in transmitted data between the at least one sensor and at least one other sensor. Furthermore, extracting at least one feature set further includes determining at least one body part motion associated with the transmitted sensor data. Furthermore, the classifying further includes categorizing a combination of the determined at least one body part motion into a classification of movements including any one of standing, walking running, jogging, kicking, dribbling, jumping, or sprinting.

The method may further include the detailed reports that also include individual movement patterns of the athlete in relation to at least one moving object and in further relation to at least one other athlete within the sporting arena. The individual movement patterns further include location and time history of the movement patterns according to the athlete's position within the sporting arena, and moving object possession patterns. The method further includes generating team movement patterns to analyze team activities within the sporting arena, wherein the team movement patterns include team coordinated patterns, moving object passing patterns, and attacking and defending patterns.

In addition, generating at least one coach decision recommendation further includes generating individual movement patterns, generating individual energy expenditure patterns, generating team movement patterns, generating a coach decision support algorithm to provide intelligent monitoring of the athlete and at least one other athlete within the sporting arena, and outputting at least one optimal decision recommendation as a function of the generated individual movement patterns, individual energy expenditure patterns, and team movement patterns to aid a coach during a sporting event. Wherein the optimal decision recommendation further includes presenting an automated playbook on a user interface, wherein the automated playbook includes at least one play, and present a generated play recommendation option on the user interface.

The method further includes wherein the generated play recommendation is generated based on the generated detailed report and further based on a pre-installed playbook, such that the generated play recommendation, and a score metric associated with highest probability of success of the play based on the detailed report statistics. Wherein the optimal decision recommendation further includes presenting a player substitution metric on a user interface, and wherein the athlete substitution metric is based at least in part on the athlete data in the detailed report. The optimal decision recommendation may further include generating coaching advice and player motivational tactics on a user interface based on the generated detailed report. And wherein the optimal decision recommendation further includes generating a game analysis report based on the generated detailed report, wherein the game analysis report further includes performance data associated with at least one athlete, a group of athletes, or an entire team, and generating a training recommendation report based at least in part on the generated detailed report.

In yet another embodiment, there is a coach decision support system including at least one data generating sensor configured to generate data associated with at least one athlete and further configured to be placed on the at least one athlete, electronic circuitry configured to collect sensor data from the at least one data generating sensor, pre-process the sensor data to filter sensor noise from the data, extract at least one feature of the collected sensor data, classify the at least one extracted feature into at least one physical activity, transmit the physical activity classification to a data analysis circuitry, generate a report of the physical activity classification indicative of a performance of the athlete within a sporting arena, and generate at least one coach decision recommendation based at least in part on the report. The coach decision support system of further includes a user-interface module configured to present at least one of an automated playbook and play recommendation, a player substitution recommendation, a coaching advice recommendation, and a game analysis and training recommendation.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 13 an illustration of a hardware description of a device according to embodiments illustrated in FIGS. 1-12.

DETAILED DESCRIPTION OF THE EMBODIMENTS

Figure 1:
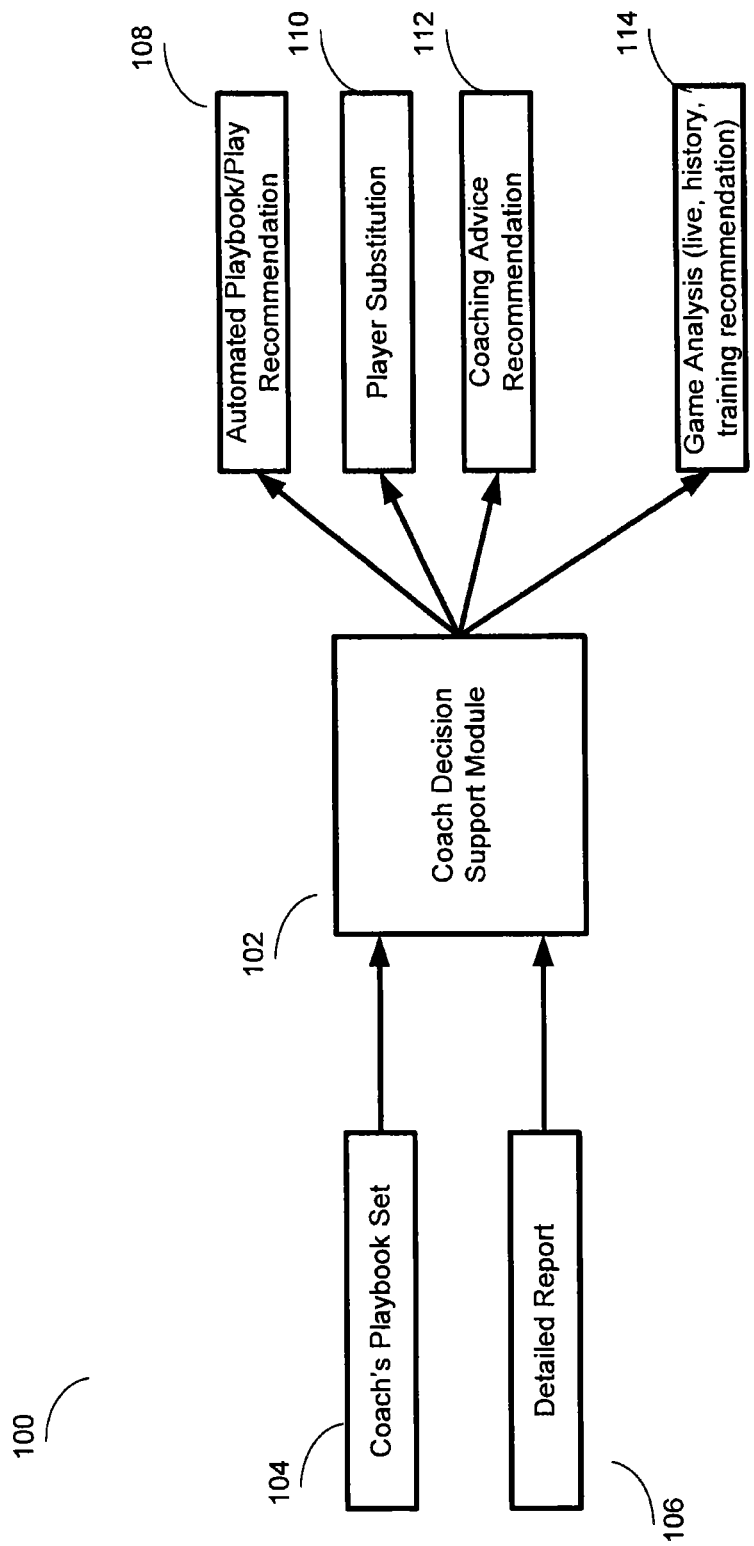
FIG. 1 is a system overview of the coach decision support system according to one embodiment.

Referring now to the drawings, wherein like reference numerals designate identical or corresponding parts throughout the several views.

FIG. 1 is a system overview of a coach decision support system 100 according to one embodiment. In this embodiment, there is illustrated the coach decision support system 100 that includes a coach decision support module (hereinafter referred to as "module") 102 that is configured to receive a series of inputs for functional manipulation and used to generate an output solution. Inputs include a coach's playbook set 104. The coach's playbook set 104 includes a series of plays used by a coach using the module (hereinafter referred to as "coach") from the coach's personal playbook. These plays can be entered manually or configured to interface with an electronic device or other module storing the plays to transfer the plays to module 102. Coach's playbook set 104 can include any play associated with the coach, the team, or known plays in the professional league. For example, coach's playbook set 104 can include plays from any given individual or team oriented sports, including but not limited to, soccer, football, volleyball, basketball, baseball, rugby, gymnastics, tennis, golf, cycling, bowling, hockey, surfing and skiing. For purposes of illustration, soccer will be used as a sport to demonstrate the capabilities of the coach decision support system.

In one embodiment, the module can be configured to receive another input related to an individual athlete or a group of athletes participating within a team sport. A detailed report input 106 is illustrative of information sent to the module that includes athlete related physical and activity information (to be discussed further below). The transmission of information may be done electronically and/or wirelessly using a wide array of technologies including but not limited to Bluetooth, WIFI, infrared, and radio frequency (RF).

Module 102 can transmit information and solutions related to several recommendations associated with coach support. In one example, module 102 can create automated playbook available for review by the coach. The automated playbook is dependent on the coach's playbook set 102 previously entered into module 102. As such, module 102 is capable of making specific play recommendations, a series of recommendations that include a series of plays, or a sequence of specific and targeted plays by an individual or a team based on the detailed report 106 received by module 102. In yet another example, module 102 can suggest player substitutions 110 to the coach based on analyzed player performance data as indicated from the detailed report 106 input. Player substitutions can be recommended if a specific player is not playing according to a team average. In yet another example, player substitutions can be recommended if the specific player is not playing up to his own standard, or is not performing up to a required standard for a performance standard, e.g., spending more time in the wrong area of the field, lacking defensively, sprinting percentages are below his usual threshold, or other parameters further discussed below.

Module 102 could also output a coaching advice recommendation 112. This feature presents a motivational aspect to a coach such that to help provide recommended words, comments, speeches, or any other subjective aspect to help provide a recommendation based on a motivational aspect. For example, if a team is down in the score but is close, coaching advice recommendation 112 may output a motivational speech, a story, a chant, or any other type of communication recommended for the coach to communicate with his players. Motivational speeches may be different depending on the scoring disparities. For example, if the coach's team is slightly ahead or slightly behind, the messages will be different than if the team was far ahead or far behind.

Module 102 is also capable of presenting game analysis and statistics 114. The game analysis will have several features, including but not limited to analysis of a singular player, an analysis of a group of players within the team and an analysis of the entire team. For example, an analysis of a singular player can focus on an offensive player, such as a striker, and map out their running paths, location frequencies, effort, energy expenditure, ball possession, shots on goal, etc. An analysis of a group of players can focus on a group, such as a defensive group of 3-5 players and analyzes their performance as a group, location frequencies, strengths and weaknesses. An analysis of the team utilizes the same analysis as above, but this is done for the entire team.

Furthermore, module 102 can store previously recorded information regarding all on field parameters. For example, module 102 can store player and team statistics from a previous game or from a series of previous games, or from an entire season. The stored statistics can be used to monitor player, group, and team progress on general or specific performance parameters. For example, the game analysis data may be used to illustrate specific player's development of a specific skill/play/coaching requirement throughout the season. Furthermore, the game analysis data can be used to generate training recommendations. Again, training recommendations can be done on an individual, group, or team levels. Training recommendations can further include statistics to show whether players missed specific assignments. For example, if a specific play is recommended to a coach and the coach selects the play. If players do not conform to the play, e.g., route 1 is not run by player x, or pass 2 is not performed by player y, then game analysis will illustrate that players x and y have specific tasks to perform during the next training session and a recommendation will be on display to the coach.

Figure 2:
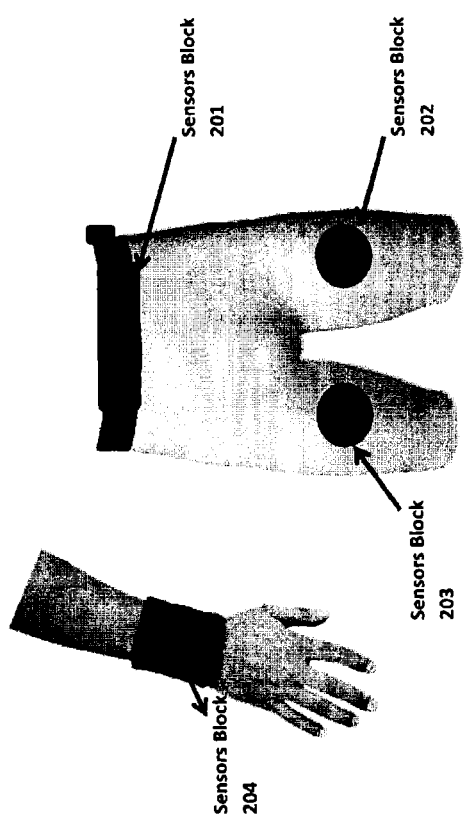
FIG. 2 is a schematic view of an athlete with various placement of sensor blocks according to one embodiment.

FIG. 2 is a schematic view of an athlete with various placements of sensor blocks according to one embodiment. Each sensor block is placed with the aim of capturing the movement of a specific muscle or body part. For example, Sensor block 201 measures motion related to the abdomen and torso of the athlete. Sensor block 201 can also measure geographic location of the athlete via Global Positioning System (GPS) technology embedded within the sensor. Sensor blocks 202 and 203 are placed on the athlete's thighs to measure specific motions. The acceleration sensor placed on the thighs of the player record the acceleration/deceleration of the legs which is helpful in classification of the activity. Such classification of the athletic activity includes running, walking, sprinting, jogging, jumping, standing as well as player to player activities such as tackling opponent athletes and kicking of a ball for example. Sensor block 204 is placed on an athlete's wrists to indicate running patterns and all hand and arm motions related to the sport. The current configuration of the sensor blocks 201-204 is but one potential configuration of a possible large combination of configurations for different sports. For example, for soccer, sensor block 204 may not be as important is it might be for tennis. Other sports may require additional sensors. For example, hand/wrist/arm/should sensor blocks may be more useful in sports such as American Football. The current illustration is yet one of many potential illustrations possible for the placement of the sensor blocks.

In yet another embodiment, sensor block 201 may further act as a shock sensor such that if the player is strongly jolted, a change in player's physical status may be more closely monitored for a period of time to detect an injury. For example, if the player subsequently starts to run more slowly or the heart rate of the player becomes elevated, showing signs of stress.

Figure 3:
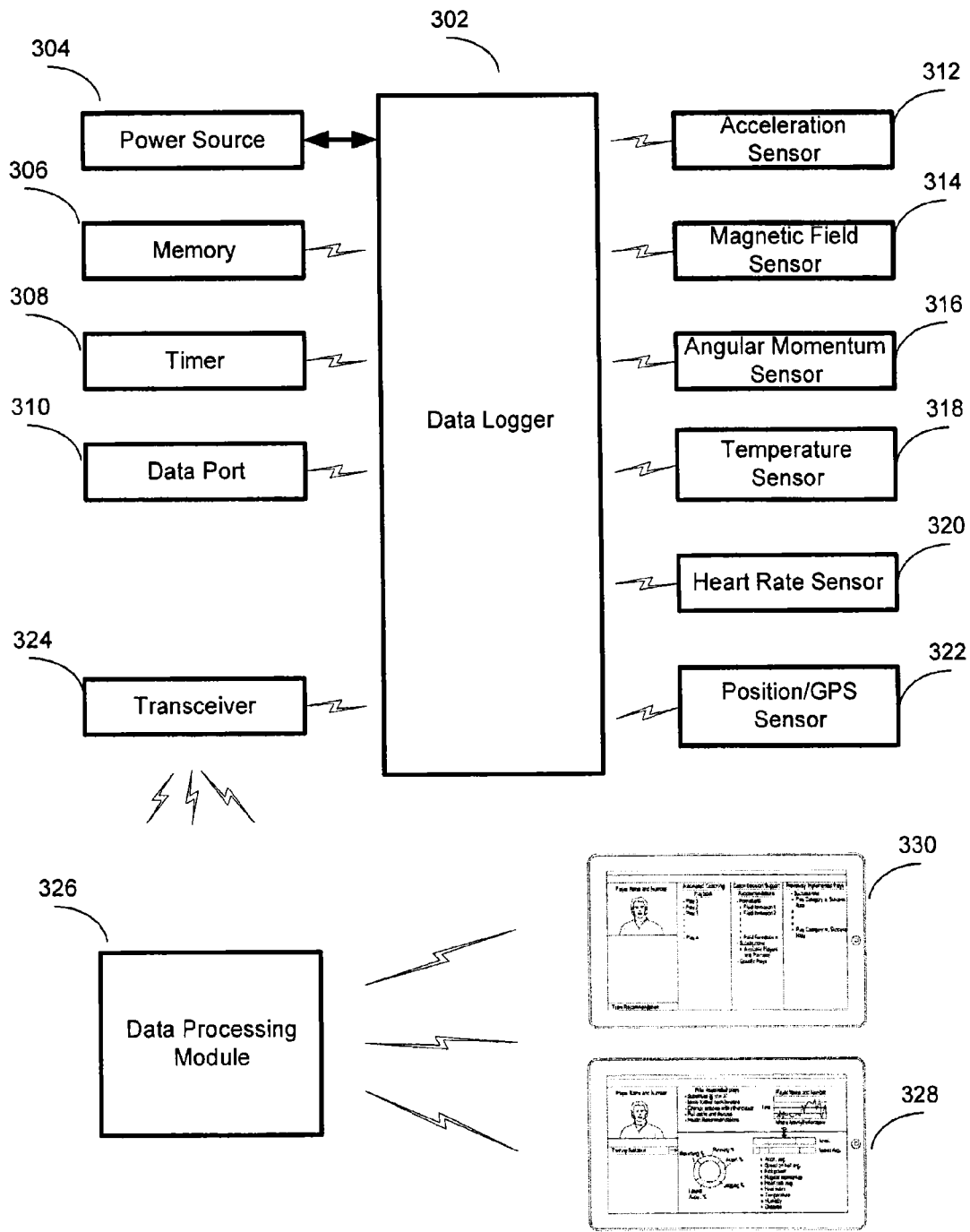
FIG. 3 is a system overview of a data logger apparatus and a given interaction configuration with different sensor blocks according to one embodiment.

FIG. 3 is a system overview of a data logger apparatus and a given interaction configuration with different sensor blocks according to one embodiment. To monitor the activities of the athlete, in real-time scenarios, an activity monitoring system is proposed, which can effectively monitory different types of activities on the ground of every individual athlete and communicate the data to a central computer for complete analysis. Data logger 302 is configured to collect and process such information. Data logger 302 may be placed as yet another sensor on the athlete, as part of a sensor assembly on the athlete (e.g., sensor block 201) or may be placed remotely. Data logger 302 includes a power source 304, memory 306, timer 308, data port 310, acceleration sensor 312, magnetic field sensor 314, angular momentum sensor 316, temperature sensor 318, heart rate sensor 320, position/GPS sensor 322 and Transceiver 324.

The power source 304 may be adapted to provide power to the data logger 302. In one embodiment, the power source 304 may be a battery. The power source may be built into the data logger 302 or removable from the data logger 302, and may be rechargeable or non-rechargeable. In an embodiment, the power source 304 may be recharged by a cable attached to a charging source, such as a universal serial bus ("USB") FireWire, Ethernet, Thunderbolt, or headphone cable, attached to a personal computer. In another embodiment, the power source 302 may be recharged by inductive charging, wherein an electromagnetic field is used to transfer energy from an inductive charger to the power source 302 when the two are brought in close proximity, but need not be plugged into one another via a cable. In some embodiment, a docking station may be used to facilitate charging. In other embodiments, the data logger 302 may be repowered by replacing one power source 302 with another power source 302.

The memory 306 may be adapted to store application program instructions and to store athletic activity data. In an embodiment, the memory 306 may store application programs used to implement aspects of the functionality of the athletic activity monitoring system described herein. In one embodiment, the memory 306 may store raw data, recorded data, and/or calculated data. In some embodiments, as explained in farther detail below, the memory 306 may act as a data storage buffer. The memory 306 may include both read only memory and random access memory, and may further include memory cards or other removable storage devices.

In some embodiments, the memory 306 may store raw data, recorded data, and/or calculated data permanently, while in other embodiments the memory 306 may only store all or some data temporarily, such as in a buffer. In one embodiment memory 306, and/or a buffer related thereto, may store data in memory locations of predetermined size such that only a certain quantity of data may be saved for a particular application of the current coach decision support module.

The timer 308 may be a clock that is capable of tracking absolute time and/or determining elapsed time. In some embodiments, the timer 304 may be used to timestamp certain data records, such that the time that certain data was measured or recorded may be determined and various timestamps of various pieces of data may be correlated with one another.

The data port 310 may facilitate information transfer to and from the data logger 302 and may be, for example, a USB port. In some exemplary embodiments, data port 302 can additionally or alternatively facilitate power transfer to power source 304, in order to charge power source 304.

A hydration sensor may also be implemented. A hydration sensor, not shown, may be further included to measure the players' temperature and sweat parameters. The hydration sensor may further include elements that include a tilt sensor on a beverage dispenser, such as a Gatorade bottle, on the sidelines that make a near field communication connection with the data logger so it provides a measurement of how many sips of a drink the athlete is taking and that information can be compared to hydration levels and playing conditions, such as temperature and humidity. This may further help provide a coded or tactile alert to the athlete if the athlete is being detected as beginning to become dehydrated.

The acceleration sensor 312 may be adapted to measure the acceleration of the data logger 302 if it is placed on the athlete or just simply sensors associated with the athlete. For example, if data logger 302 is physically coupled to an object (such as an athlete as shown in FIG. 2 or a piece of athletic equipment (not shown)), the acceleration sensor 312 may be capable of measuring the acceleration of the athlete, including the acceleration due to the earth's gravitational field. In one embodiment, the acceleration sensor 312 may include a tri-axial accelerometer that is capable of measuring acceleration in three orthogonal directions. In other embodiments one, two, three, or more separate accelerometers may be used.

The magnetic field sensor 314 may be adapted to measure the strength and direction of magnetic fields in the vicinity of the data logger 302. Accordingly, when the data logger 302 is physically coupled to an athlete or a piece of athletic equipment, the magnetic field sensor 314 may be capable of measuring the strength and direction of magnetic fields in the vicinity of the athlete, including the earth's magnetic field. In one embodiment, the magnetic field sensor 314 may be a vector magnetometer. In other embodiments, the magnetic field sensor 314 may be a tri-axial magnetometer that is capable of measuring the magnitude and direction of a resultant magnetic vector for the total local magnetic field in three dimensions. In other embodiments one, two, three, or more separate magnetometers may be used.

In one example, the acceleration sensor 312 and the magnetic field sensor 314 may be contained within a single accelerometer-magnetometer module bearing model number LSM303DLHC made by STMicroelectronics of Geneva, Switzerland. In other embodiments, the data logger may include only one of the acceleration sensor 312 and the magnetic field sensor 314, and may omit the other if desired.

The angular momentum sensor 316, which may be, for example, a gyroscope, may be adapted to measure the angular momentum or orientation of the data logger 302. Accordingly, when the data logger 302 is physically coupled to an athlete or athletic equipment, the angular momentum sensor 316 may be capable of measuring the angular momentum or orientation of the athlete. In one embodiment, the angular momentum sensor 316 may be a tri-axial gyroscope that is capable of measuring angular rotation about three orthogonal axis. In other embodiments one, two, three, or more separate gyroscopes may be used. In an embodiment, the angular momentum sensor 316 may be used to calibrate measurements made by one or more of the acceleration sensor 312 and the magnetic field sensor 314.

The temperature sensor 318 may be, for example, a thermometer, a thermistor, or a thermocouple that measures changes in the temperature. In some embodiments, the temperature sensor 318 may primarily be used for calibration other sensors of the athletic activity monitoring system, such as, for example, the acceleration sensor 312 and the magnetic field sensor 316. In other embodiments, the temperature sensor 318 may be used to calculate the energy expenditure of an athlete.

The heart rate sensor 320 may be adapted to measure an athlete's heart rate. The heart rate sensor 320 may be placed in contact with the athlete's skin, such as the skin of the athlete's chest, and secured with any strapping mechanism. The heart rate sensor 320 may be capable of reading the electrical activity the athlete's heart.

The position/GPS sensor 322 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the position/GPS sensor 322 may be an antenna that is capable of communicating with local or remote base stations or radio transmission transceivers such that the location of data logger 302 may be determined using radio signal triangulation or other similar principles. In some embodiments, position/GPS sensor 332 data may allow data logger 302 to detect information that may be used to measure and/or calculate position waypoints, time, location, distance traveled, speed, pace, or altitude.

The transceiver 324 may enable the data logger 302 to wirelessly communicate with other components of the coach decision support system 100, such as those described in further detail below. In one embodiment, the data logger 302 and the other local components of the coach decision support system 100 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for a coach decision support system 100 may also be used.

In one embodiment, transceiver 324 is a low-power transceiver. In some embodiments, transceiver 324 may be a two-way communication transceiver 324, while in other embodiments transceiver 324 may be a one-way transmitter or a one-way receiver. Wireless communication between data logger 302 and other components of the coach decision support system 100 is described in further detail below. In other embodiments, the data logger 302 may be in wired communication with other components of the coach decision support system 100 that does not rely on transceiver 324.

Once data logger 302 collects all sensor data associated with an athlete or a group of athletes, the data may be forwarded to data processing module 326. Data processing module 326 may be configured to process and house a variety of information for dissemination to multiple user interface devices such as devices 328 and 330 as will be further discussed below. Data processing module 326 may be configured to be a part of the data logger 302, or alternatively, data logger may be configured to be integrated within data processing module 326. Furthermore, data processing module 326 may be configured to be integrated within a server or a central server that is enabled to perform certain processing functions, such as processing the data received from data logger 302.

Coach decision support system 100 may further include features that enable the data processing module 326 to interact with web based systems to retrieve player related statistics. For example, data processing module 326 may be configured to connect to and process data from a single data logger or a specified number of data loggers associated with team athletes. However, in order to perform specific data manipulations and comparisons on a league wide basis, data processing module may be further configured to connect to internet based system to download other player/team information. This is useful in determining own team performance against an opposing team, either after playing to help in preparation for training or before playing to help in modification of plays for example.

Figure 4:
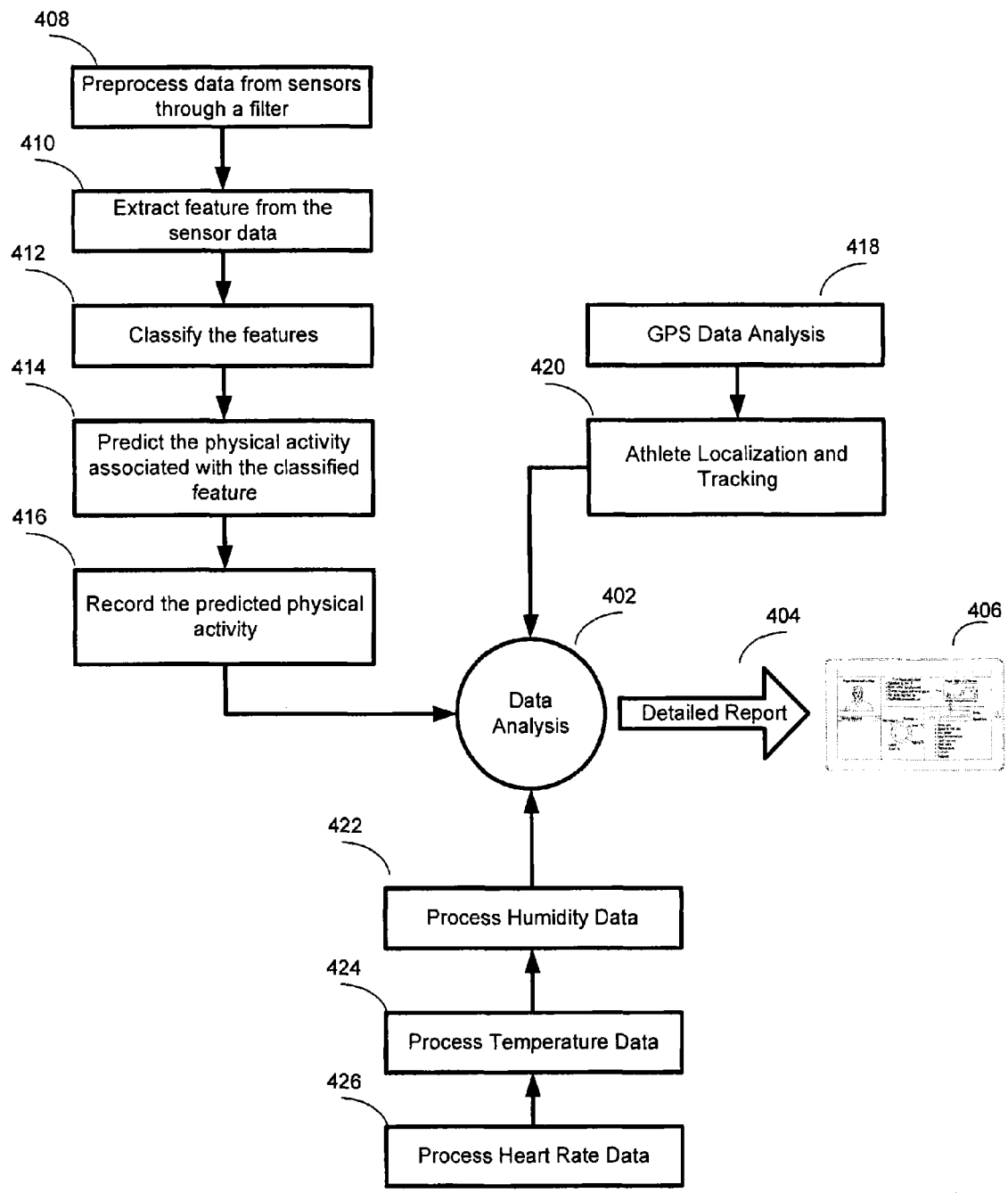
FIG. 4 is a flow chart illustrating a sample algorithm to classify and predict physical activity of an athlete according to an embodiment.

FIG. 4 is a flow chart illustrating a sample algorithm to classify and predict physical activity of an athlete according to an embodiment. In one embodiment, data processing module 326 receives data from data logger 302 and performs a data pre-processing operation on the data. Data processing module 326 may include a data analysis module 402 to process all the received data and issue a detailed report 404 to user interface. Data pre-processing operation 408 can include filtering the data signal from data logger 302 to remove all noise associated with the signals and reduce interference from other data loggers/sensors in the vicinity.

Once the data signal has been pre-processed, data analysis module 402 moves to extract features 410 associated with each recorded athlete data. For example, feature extraction may include features and motions associated with specific activities. For example, a walking activity may be associated with a different activity than a standing or running activity. As such, feature extraction allows for extraction of all relevant physical features associated with the athlete. After extracting the features, data analysis module 402 classifies 412 the features into specific activities. Such activities include, but are not limited to, walking, running, sprinting, standing, jogging, dribbling, passing, and so on. The classified activities are recorded in real time and passed on for additional data analysis.

In one example, acceleration signals are recorded by the sensors placed on thighs and waist of an athlete. Before calculating any feature, the raw accelerometer and gyro data is pre-processed to reduce noise using median filter or an order n filter in each dimension separately. A window of $w_t$ seconds ($f_s \times w_t$ samples) is used to calculate the feature set for a particular activity. Here, for example, $f_x$ is the sampling frequency of the data. In one example, there will be a time series recorded from acceleration sensors and gyro sensors from different sensor modules placed on the athlete. A plurality of features is extracted from these time series. Such features include time domain features, such as mean, standard deviation, moments, minimum and maximum values, signal magnitude area, correlation coefficients and the like. There are also frequency domain features, such as mean frequency, energy of frequency bands and the like. Once appropriate and relevant features are calculated from signals, a classifier will be optimized to classify different physical activities using this feature set. The classifier may include nearest neighbor classifier, neural network classifier or ensemble classifier whichever shows better classification accuracy. Such classifier methodology can be further referenced in (Arif, M. et al. *Better Physical Activity Classification using Smartphone Acceleration Sensor*. Journal of Medical Systems 38:95, 2014, incorporated herein by reference).

After classifying 412 the features, data analysis module 402 may predict 414 the physical activity associated with the classified feature. For example, walking may utilize specific features, wherein jogging may utilize the same features (leg, arm or other body part movements) but in more intense manners. As such, data analysis module 402 may predict 414 the physical activity, e.g. walking, running, jogging, hiking, etc., associated with the classified feature, e.g. specific muscle movements. In one embodiment, the predicted physical activity is recorded 416 in real time and readied to be transmitted to user interface or device 406.

In yet another embodiment, other data may further be processed along with the feature classification and prediction discussed above. Such data may include, for example, GPS data. Data analysis module 402 may analyze 418 GPS data received from the data logger 302 along with any athlete localization and tracking information 420. Data analysis module 402 may further process humidity data 422, temperature data 424 and heart rate data 426. After an analysis is carried out, data analysis module 402 produces a detailed report 404 to the user interface or mobile device 406 for additional manipulation and display for a coach or staff member or any other user.

Figure 5:
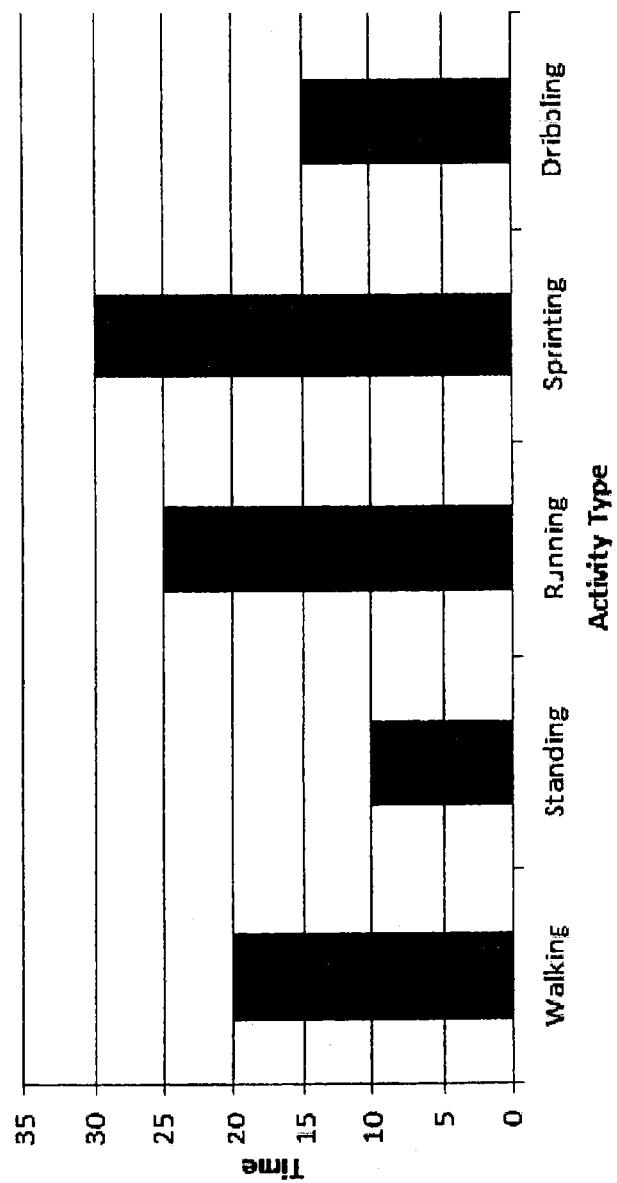
FIG. 5 is a sample activity type plot versus time for a given athlete according to one embodiment.

FIG. 5 is a sample activity type plot versus time for a given athlete according to one embodiment. For example, the graph may illustrate the athlete's physical activity performed over a period of time or as a percentage of the total time spent on the field. For example, data of an athlete being analyzed can illustrate that the athlete was walking 20% of the match time, standing 10% of the match time, Running 25% of the match time, sprinting 30% of the match time and dribbling 15% of the match time. Other plots may be generated, including geographic location of the athlete, other activities, and other statistics, such as but not limited to, side to side motions, zone coverage areas and percentage presence within specific zones, and other performance parameters, such as scoring statistics and dribbling and passing statistics. Other statistics may also include field occupancy grid that illustrates the time spent by the player on a particular place on the field according to his position. Individual movement patterns are key to coaching decision regarding plays, routs, and substitutions. Classification of movements, such as standing, walking, running, jogging, kicking, dribbling, and jumping, amongst others, allows the coach decision support system to track individual movement patterns. Location and time history of the movement patterns according to the athlete's position in the field are also recorded by the coach decision support system, including sprinting patterns and ball possession and passing patterns.

Calculating individual energy expenditure patterns are yet another key embodiment that allows the coach decision support system to aid a coach decision making process. Performance of the player heavily depends on the environment temperature and humidity levels. Individual energy expenditure patterns are calculated from the player movement patterns and intensity of the patterns will be modified by temperature and humidity of the environment. Physical performance of the players may decrease with the environmental conditions of the game due to thermal stress on the player. As such, information such as individual energy expenditure patterns is important to a coach. Furthermore, individual energy expenditure patters will be available to a coach live during an athletic event and also as report at the end of an athletic event. The individual energy expenditure patterns will help the coach decide how much time an athlete should stay in the field and when he has to be replaced to optimize the match results. Furthermore, the individual energy expenditure patters will also aid the coach decision support module in outputting recommendations to a coach on what substitutions are necessary and why, what plays are necessary and why, and what are the optimum solutions presented to provide the optimum results.

In yet another example, the coach decision support system 100 may provide a distribution of activity graph for every player and the whole team during and after the match. These graphs, as illustrated in FIG. 5 may include total time of physical activities and frequency of the physical activities. Furthermore, quality of high intensity activities depends on distance and duration of the activity, and ability to repeat these activities. Providing this information to the coach may help the coach analyze the performance of each player. Alternatively, coach decision support system 100 may analyze the information of each player and team on behalf of the coach and put out a set of recommendations of how to best move forward.

In another example, total distance and ground occupancy covered by each individual player and all the players may further be provided. The coach decision support system 100 may further provide distance covered in different types of activities and different speed zones, colored graph of ground occupancy of every player. The coach decision support system 100 may further provide relative moment graphs of different players. For example, a coach may select a specific player or group of players and can see his or their relative movement on the field. This may help to design the attacking or defending moves of the player on the field and may confirm the execution of different game plans.

Figure 6A:
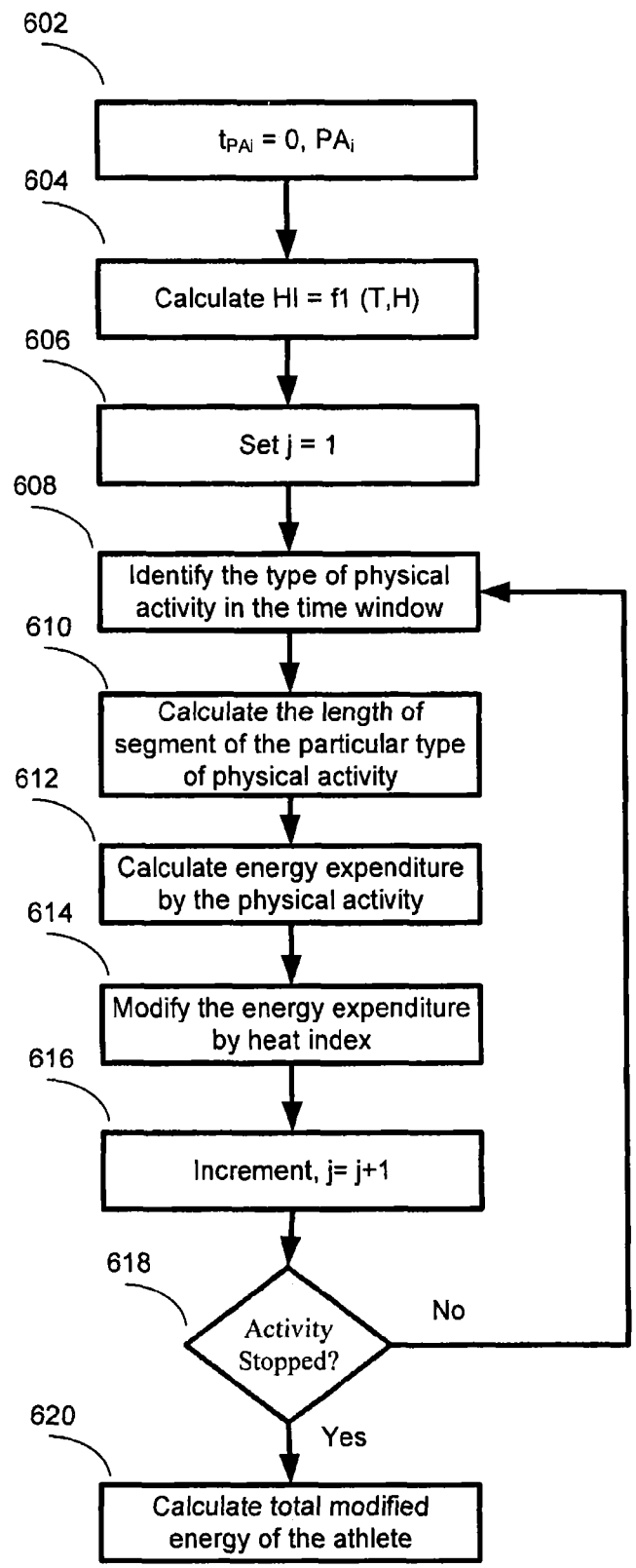
FIG. 6a is a flow chart illustrating a sample algorithm to calculate the energy expenditure of an athlete according to an embodiment.
Figure 6B:
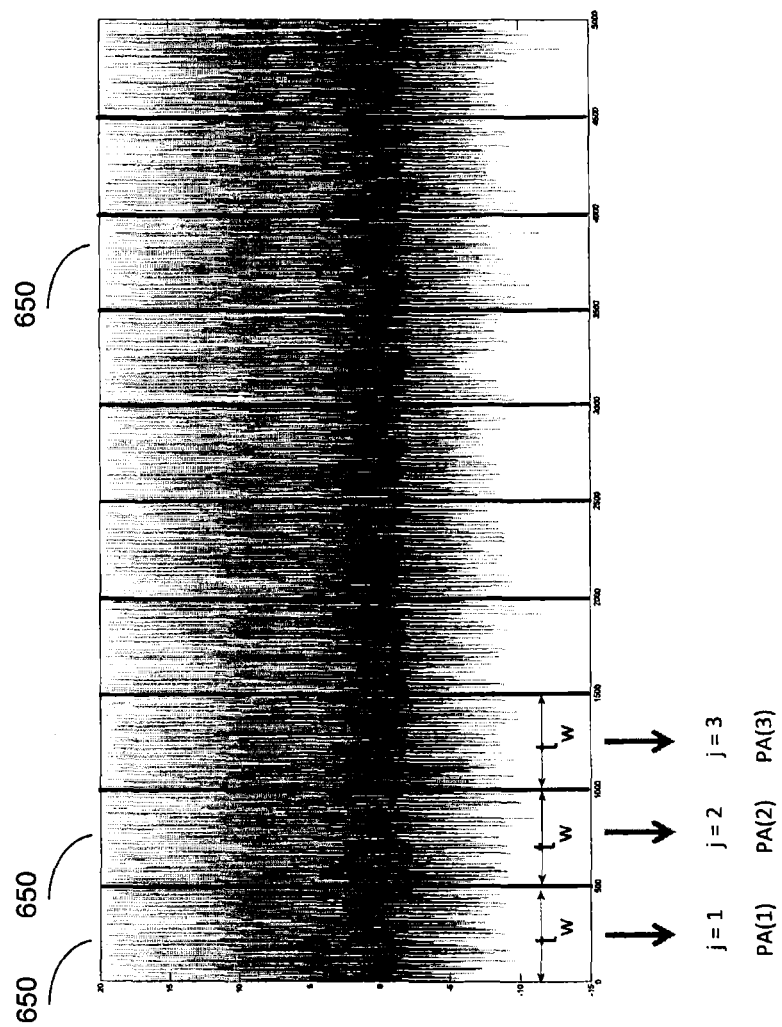
FIG. 6b is a data sampling illustration to generate window sizes for sampling sensor data within the specified window according to an embodiment.

To illustrate the individual energy expenditure pattern calculation further, FIGS. 6a and 6b demonstrate a flow chart illustrating a sample algorithm to calculate the energy expenditure of an athlete according to an embodiment and a data sampling window. The algorithm utilizes a series of equations to measure the energy expenditure of a player. Table 1 below illustrates a set of definitions utilized in the equations.

TABLE 1

Definitions of Energy Expenditure Calculation Equations

| | |
|---|---|
| PA | All types of physical activities of the player in the ground like Standing, Walking, Running, etc |
| T | Temperature |
| H | Humidity |
| HI | Heat Index |
| $PA_i(t)$ | $i^{th}$ Physical Activity of the player at time t |
| t | Time variable |
| $t_w$ | Time window to calculate the physical activity |
| MEn | Modified energy expenditure taking into account of heat index |

As an initial step, the physical activity of the player may be initialized 602 to zero, that is to zero out the $i_{th}$ physical activity of the player at time t as follows:

$$t_{PA_i}=0, \forall PA_i \quad (1)$$

This enables the system to start fresh, select the specific physical activity of the player and begin to calculate 604 a heat index as a function of temperature and humidity measured at the data logger 302;

$$HI=f_1(T,H) \quad (2)$$

The next step is to set 606 a value $j$ to $1j=1$ \quad (3)

In the algorithm, real time sensor data may be recorded continuously. As such, a window size $t_w$ is defined. Based on this window size a subset of sensors data will be taken and based on this data, type of physical activity is calculated. It can be explained by FIG. 6b. The data coming from sensors will be divided by the window size 650 and the sensor data within this window 650 will be used by the function to calculate the type of the physical activity. For example, the counter j is used for the physical activity for a particular data in the window. For example for j=1, physical activity may be "standing" and for j=2, the physical activity may be "running" etc.

In referring back to FIG. 6a, the step of setting a value for j is followed by identifying 608 the type of physical activity in the time window, $$PA_i(j)=\text{Identify\_PA}(Acc(t_w), GPS(t_w)) \quad (4)$$

Calculate 610 the length of segment of the particular type of physical activity.

$$\text{if } PA_i(j)=PA_i(j-1), t_{PA}=t_{PA_i}+t_w \quad (5)$$

Calculate 612 energy expenditure by the physical activity $$En^{tw}=\text{Calculate\_Energy\_Expenditure}(PA_i(j), t_w) \quad (6)$$

Modify 614 the energy expenditure by heat index $$MEn(j)=f_2(En^{tw}, HI) \quad (7)$$

Increment 616, $j=j+1$ \quad (8)

The next step is to check 618 the stopping criteria of the player or athlete. If the athlete has not stopped yet, then then attempt to identify another type of physical activity in the time window as illustrated in equation (4) above, otherwise move to calculate 620 total modified energy of the player;

$$MEn=\Sigma_j MNe(j) \quad (9)$$

Figure 7:
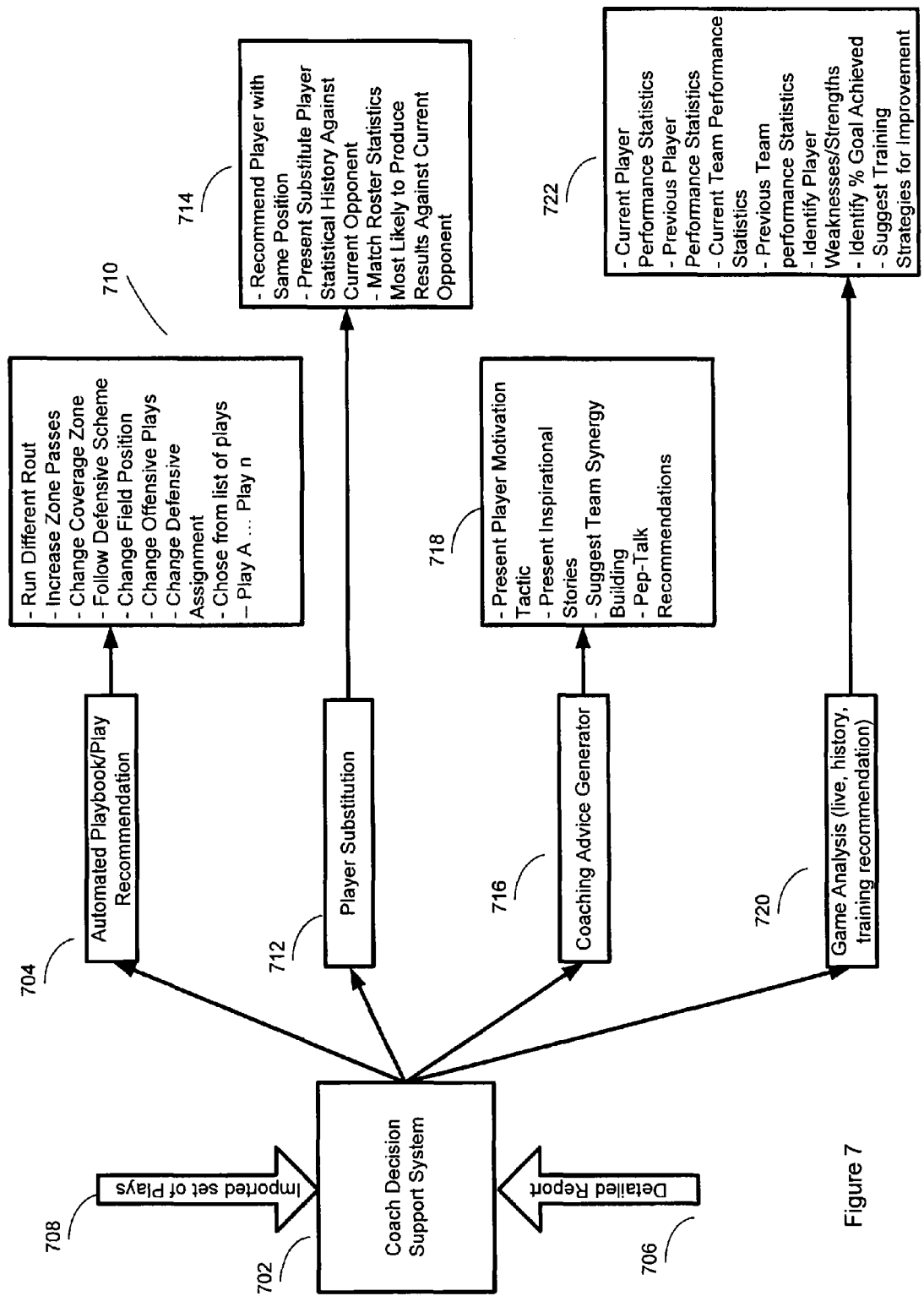
FIG. 7 is an illustration of a sample coach decision support system capabilities presented to a coach according to an embodiment.

FIG. 7 is an illustration of a sample coach decision support system capabilities presented to a coach according to an embodiment. Once the athlete data is classified and physical activities are predicted, the coach decision support system can be configured to output a series of solutions to help aid the coach in making key coaching during a live event such as a match or a game, or to help develop additional training options.

In one embodiment, coach decision support system 702 may transmit information and solutions related to several recommendations associated with coach support. In one example, coach decision support system 702 may create automated playbook 704 available for review by the coach. The automated playbook 704 is dependent on the coach's playbook set 102 previously entered into module 102. As such, coach decision support system 702 is capable of making specific play recommendations, a series of recommendations that include a series of plays, or a sequence of specific and targeted plays by an individual or a team based on the detailed report 706 and imported set of plays 708 received by module 102, which is part of coach decision support system 702. Box 710 illustrates a sample list of options available to a coach and a sample set of plays that a coach may have already included in his play book. For example, one play my be to task a specific athlete to run a different route, increase passes within a specific zone, change coverage to a different zone (for example from midfield to defense, or vice versa) or even follow a specific pre-discussed defensive scheme. Such defensive scheme may include a zone type of scheme, a tag team type of scheme or an individual one-to-one type of scheme or any other combination thereof. Another example of a play recommendation that may be produced by the coach decision support system 702 is to change the field position of the player (e.g., right to left), change offensive plays (such as more through passes and less lobs) or change defensive assignments (such as switch covered players, or different zones). Another example may be present a list of automated plays from the pre-stored automated playbook and allow the coach to review a set of plays from his playbook. Another example may be to present the coach with top plays that are best suited in view of the player performance data received from the detailed report 706. For example, plays "increase zone passes", "increase through passes" or "increase lob passes" might be of higher priority than others depending on the player performance information received in the detailed report. Other plays, such as "change coverage zone" might take higher precedent than "follow defensive scheme x" if, for example, the player information in the detailed report indicate that the player energy expenditure levels are above a certain level.

In yet another example, coach decision support system 702 can suggest player substitutions 710 to the coach based on analyzed player performance data as indicated from the detailed report 706 input. Player substitutions can be recommended if a specific player is not playing according to a team average. In yet another example, player substitutions can be recommended if the specific player is not playing up to his own pre-measured standard, or is not performing up to his own measured practice standard, or is not performing up to a required standard for a performance standard, e.g., spending more time in the wrong area of the field, lacking defensively, sprinting percentages are below his usual threshold, or other parameters. Box 714 illustrates a sample list of options available to a coach and a sample set of recommended player substitutions. Coach decision support system 702 may recommend a substitute player in the same position, present a substitute player statistical history, present a substitute player statistical history against a current opponent if data exists, or present an optimum roster statistics most likely to produce results against the current opponent. For example, a roster match my include a most effective combination of players best suited to take on the current opponent at that time of the match, given statistical analysis of the detailed report 706.

One performance parameter of an athlete depends on the energy expenditure on the field. Every player has to perform different types of physical activities which may be low intensity or high intensity, such as passing and sprinting respectively. Recovery time between high intensity moves may prolong the performance of the player. Thus it is important to change the players with optimal changing time to keep the performance of the players at their best. As such, one feature of the player substitution recommendation is that the coach decision support system 702 may provide feedback to a coach about the optimal time of changing players and suggesting their rest times. Heart rate data will also help to predict the performance of the player. Heart rate data can also provide information related to heart rate variability in different types of activities. Such information may also help in optimizing the training sessions Coach decision support system 702 may also provide a coaching advice recommendation 716. This feature presents a motivational aspect to a coach such that to help provide recommended words, comments, speeches, or any other subjective aspect to help provide a recommendation based on a motivational aspect. For example, if a team is down in the score but is close, coaching advice recommendation 716 may output a motivational speech, a story, a chant, or any other type of communication recommended for the coach to communicate with his players. Motivational speeches may be different depending on the scoring disparities. For example, if the coach's team is slightly ahead or slightly behind, the messages will be different than if the team was far ahead or far behind. Box 718 illustrates a sample list of options available to a coach such as present a player motivation tactic to a coach to deliver to players if a specific player or group of players is noticeably performing below their average. For example, if player X has been previously measured, in previous matches or in a previous sporting event, to run a specific distance per match, or run at given speeds, or sprint a specific percentage of his performance, and the current measured values are significantly below those levels, then a flag may be raised to the coach's attention and a recommendation is presented in the form of, as listed before, a set of plays, or in this case, a let of motivational tools as presented in box 718.

Coach decision support system 706 may also present game analysis and statistics 720 to a coach. The game analysis will have several features, including but not limited to analysis of a singular player, an analysis of a group of players within the team and an analysis of the entire team. For example, an analysis of a singular player can focus on an offensive player, such as a striker, and map out their running paths, location frequencies, effort, energy expenditure, ball possession, shots on goal, etc. An analysis of a group of players can focus on a group, such as a defensive group of 3-5 players and analyzes their performance as a group, location frequencies, strengths and weaknesses. An analysis of the team utilizes the same analysis as above, but this is done for the entire team.

In one embodiment, coach decision support system 702 may further include camera system (not shown) that can detect movement and activity levels of other team members. For example, the camera system could detect zone defense vs. man to man defense schemes and make a recommendation play based on the defense's configuration. The camera system may analyze own player and own team members or alternatively analyze opposing team members or both teams on the field. Additionally, the camera system may detect a number of substitutions performed by the opposing team and make recommendation. For example, if the opposing team greater or fewer amount of substitutions, it can be indicated that they other team members are tired and the coach decision support system 702 may recommend a play that will require the defense to expand a lot of energy.

In yet another example, coach decision support system 702 can store previously recorded information regarding all on field parameters. For example, coach decision support system 702 can store player and team statistics from a previous game or from a series of previous games, or from an entire season. The stored statistics can be used to monitor player, group, and team progress on general or specific performance parameters. For example, the game analysis data may be used to illustrate specific player's development of a specific skill/play/coaching requirement throughout the season. Furthermore, the game analysis data can be used to generate training recommendations. Again, training recommendations can be done on an individual, group, or team levels. Training recommendations can further include statistics to show whether players missed specific assignments. For example, if a specific play is recommended to a coach and the coach selects the play. If players do not conform to the play, e.g., rout 1 is not run by player x, or pass 2 is not performed by player y, then game analysis will illustrate that players x and y have specific tasks to perform during the next training session and a recommendation will be on display to the coach.

Figure 8:
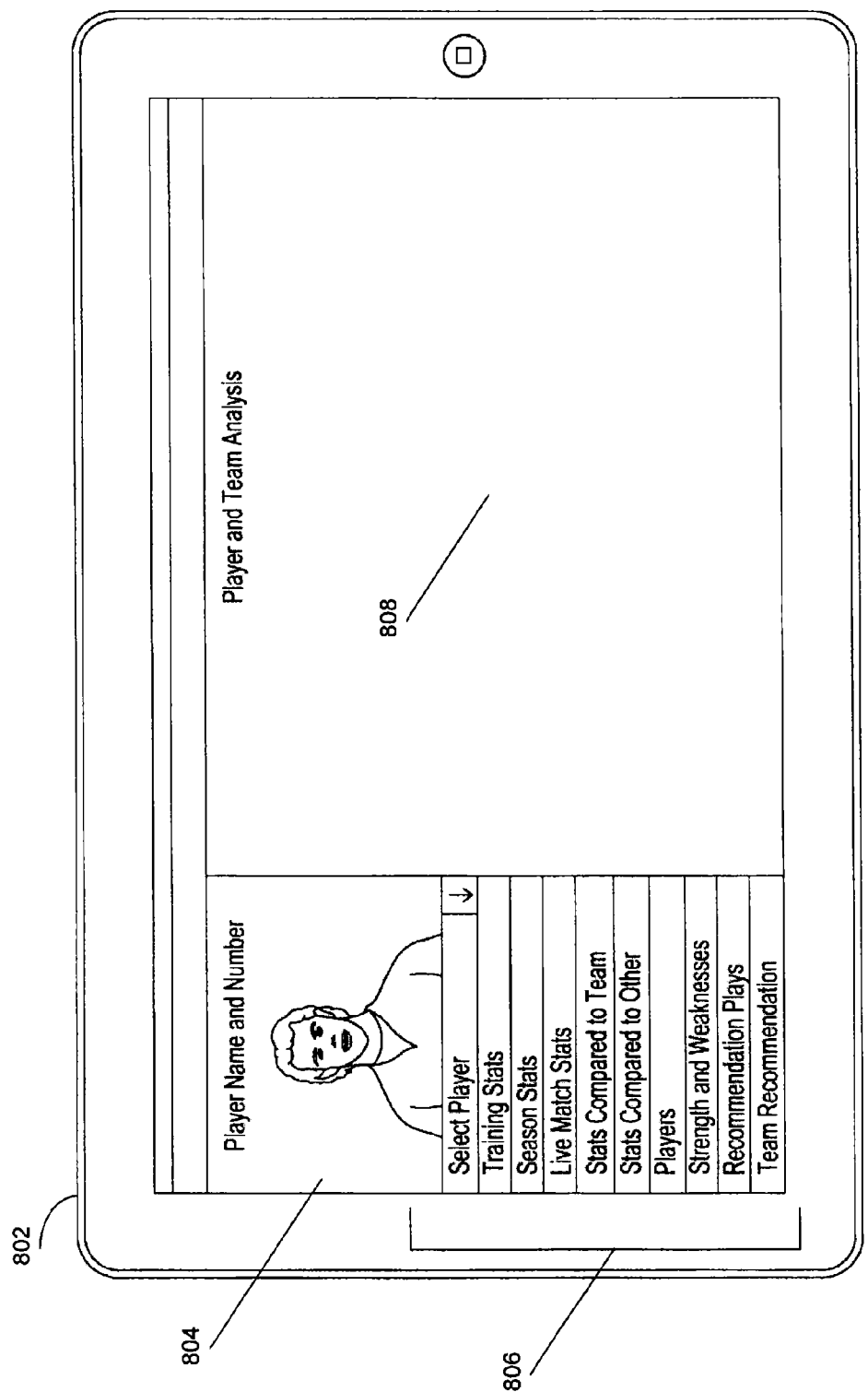
FIG. 8 is an illustration of a coach decision support system user interface according to one embodiment.

FIG. 8 is an illustration of a coach decision support system user interface according to one embodiment. User interface 802 may be presented on any interactive device or mobile device, such as a smart phone or a touch pad or a touch computer device. Interface 802 may include a set of menu items 804 for a coach to select and manipulate. Menu items may include several options for the coach to view data and manipulate the data, such as player selection, training statistics, season statistics, live match statistics, statistics of the player compared to the team, statistics of the player compared to another player, statistics of the player compared to other players not on the roster, such as an opponent player, strengths and weaknesses of the player, recommendation plays, and team recommendations. Other options may also be presented to manipulate the measured and collected data. For each selected player, the player name, number and photo identification are presented in window 806. Interface 802 may further include a player and team analysis window 808. Window 808 may be configured to illustrate graphically the analyzed and processed data from the various sensors as will be shown further below.

Figure 9:
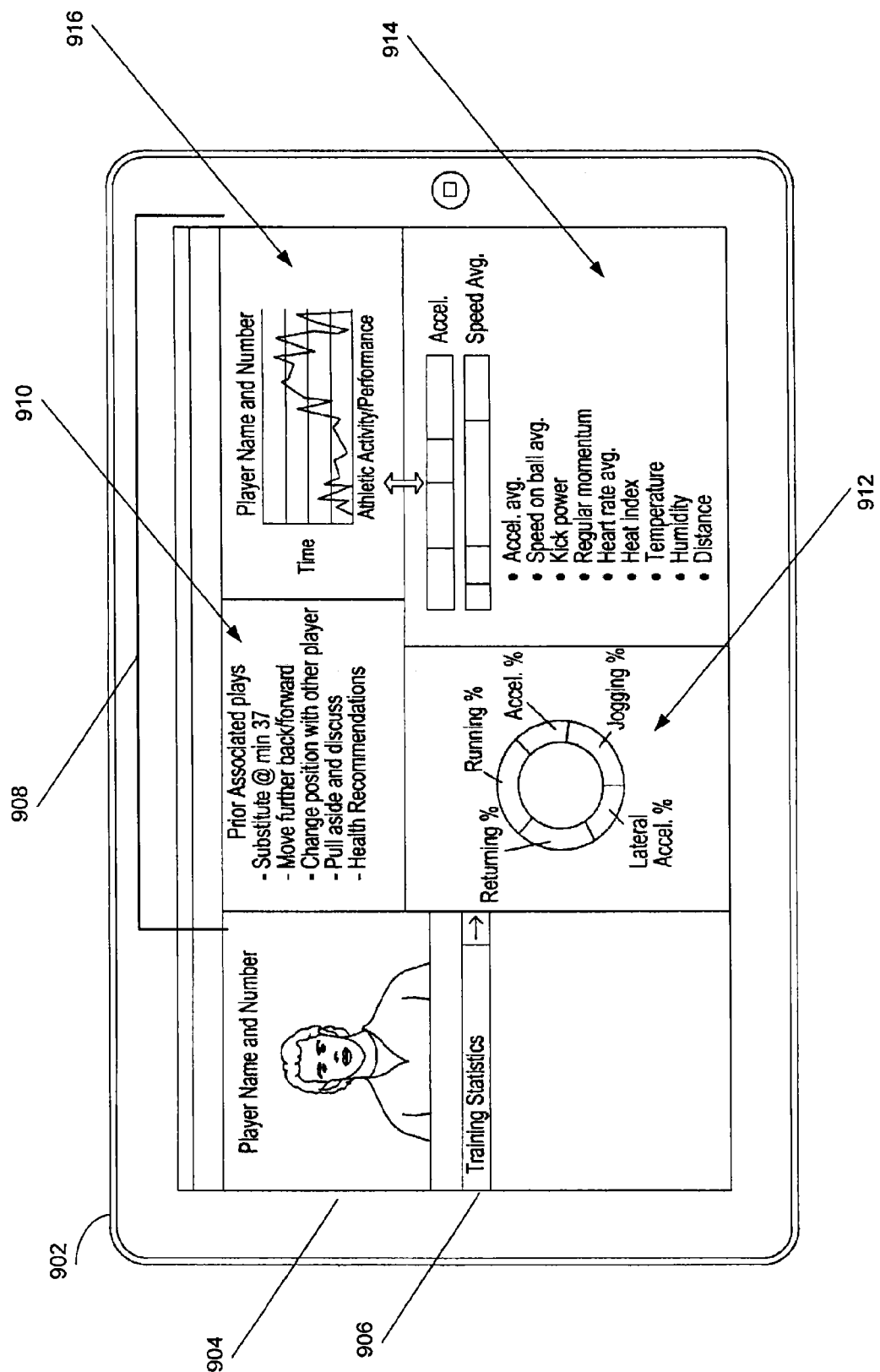
FIG. 9 is an illustration of a coach decision support system user interface displaying statistics associated with an athlete according to another embodiment.

FIG. 9 is an illustration of a coach decision support system user interface displaying statistics associated with an athlete according to another embodiment. Interface 902 includes the selected player name and number and profile photo 904. Furthermore, as an illustrative example, training statistics 906 are selected for this particular player and the player/team analysis window 908 includes a variety of metrics available to the coach. Player/team analysis window 908 may include a display of prior associated plays 910. Prior associated plays 910 may be a listing of recorded plays specifically run for the selected player shown in window 904. For example, it may be known that this player expands a large amount of energy early on in a match, as such, prior associated play or strategy may be to substitute this player at a predetermined time, for example at minute 37. Alternatively, it may be known that this player has specific tendencies to leave his zone and go forward or backwards, as such a recommendation to move the player further forward or backwards may further be displayed as a previously deployed option or play. Each player may further have a set of health recommendations and records viewable to the coach. For example, the coach may need to know health record of a specific player to know when the player was last sick or when the player may need to take on any special medication, or any known or previously recorded injuries.

In yet another embodiment, player/team analysis window 908 may further include a graphical illustration or distribution activity graph 912 illustrating the percent physical activity performed by the player. For example, the selected player may be running a given percentage of the time, while accelerating a different percentage of the time. Other parameters include a wide array of physical activities, including but not limited to running, walking, sprinting, dribbling, lateral acceleration, returning back, and so on. This window may graphically illustrate to a viewer or coach with an immediate glance, what the player is doing, what are his most frequent activities, what percentage of the time is he spending on a given physical activity, such as sprinting. Distribution activity graph 912 may further include a total number of distance covered by the player (not shown), an energy expenditure level index (not shown) or any other relevant parameter to the coach to view at first glance.

Another window within the player/team analysis window 908 may be a secondary activity graph window 914 that illustrates performance and surrounding environmental measurement data, such as humidity, temperature, heat index, heart rate average. Window 914 may further include player related metrics, including kick power, shots on goal, speed on ball, speed on ball average, acceleration, acceleration average, distance covered and the like. This window may be configurable to be further illustrative by showing numbers and percentages, and/or alternatively, by showing graphical illustrations. Player/team analysis window 908 may further include an analysis window 916 that may graphically illustrate player performance in time. For example, for a selected player, an athletic activity is measured as a function of time, such that as time progresses, the coach can view an illustration of the player's activity performance over a period of time. For example, a player may be sprinting more during the beginning minutes of a match, but then the frequency of his sprinting capacities may be in decline as the match progresses.

Figure 10:
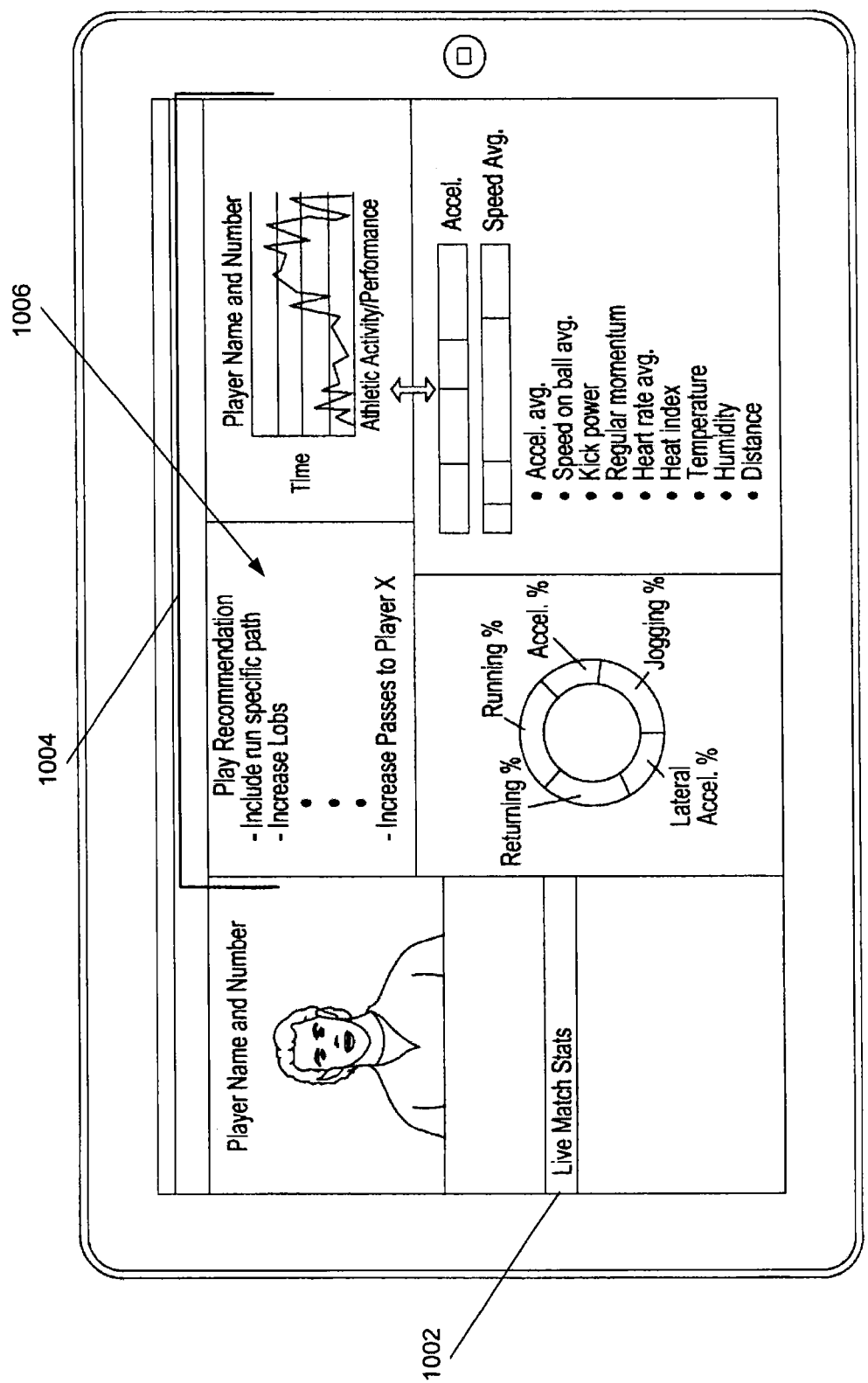
FIG. 10 is an illustration of a coach decision support system user interface displaying live match statistics of a selected athlete according to an embodiment.

FIG. 10 is an illustration of a coach decision support system user interface displaying live match statistics of a selected athlete according to an embodiment. In one example, a different option from the menu may be selected, such as live match statistics 1002. Selecting live match statistics 1002 will illustrate the live match statistics for the selected player in real time as they are recorded by data logger 302. Player/team performance window 1004 will reflect the selected menu option 1002 and display all live statistics or statistics up to that point in time. Player/team performance window 1004 may further display a play recommendation window that displays a list of recommended plays based on the measured parameters indicated previously. For example, recommended plays may include running specific paths, increasing lobs or through passes, or increasing passes to a selected or star player.

Figure 11:
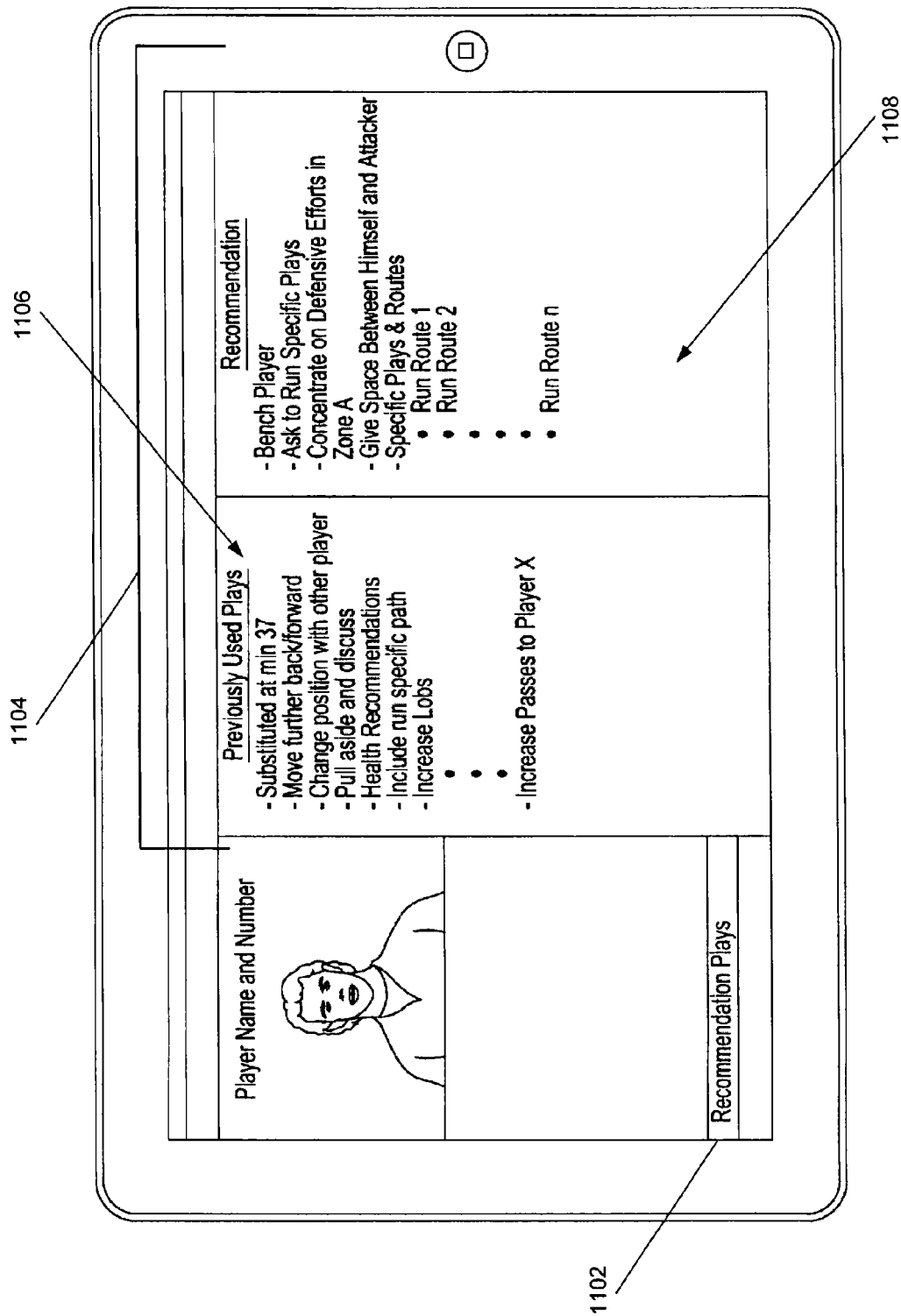
FIG. 11 is an illustration of a coach decision support system user interface displaying a history of recommended plays and a list of current coach decision recommendations according to an embodiment.

FIG. 11 is an illustration of a coach decision support system user interface displaying a history of recommended plays and a list of current coach decision recommendations according to an embodiment. In one example, a coach may select menu option for recommendation plays 1102, at which point the player/team performance window 1104 will display a variety of options viewable to the coach. One such option includes previously used plays 1106. This option enables the coach to review previously used plays and their success rate. It may serve as a good reminder to the coach of what plays was run. For example, such plays may include a time in which the specific player was substitute, places where the player was moved, positions in which the player was changed to, discussions in which the coach discussed with the player, health related records and recommendations, specific paths and plays run before, and increasing passes to other players. This list is just an illustrative list of the many possible previously used plays that will depend on each coach's prior recorded decisions.

In another example, player/team performance window 1104 may further include current recommendations 1108 available to the coach. As an illustrative example, such recommendations may include benching the player, asking the player to run specific routs, concentrate on defensive efforts, stay within a given zone, choose new spacing options, or running specific plays or routs.

Figure 12:
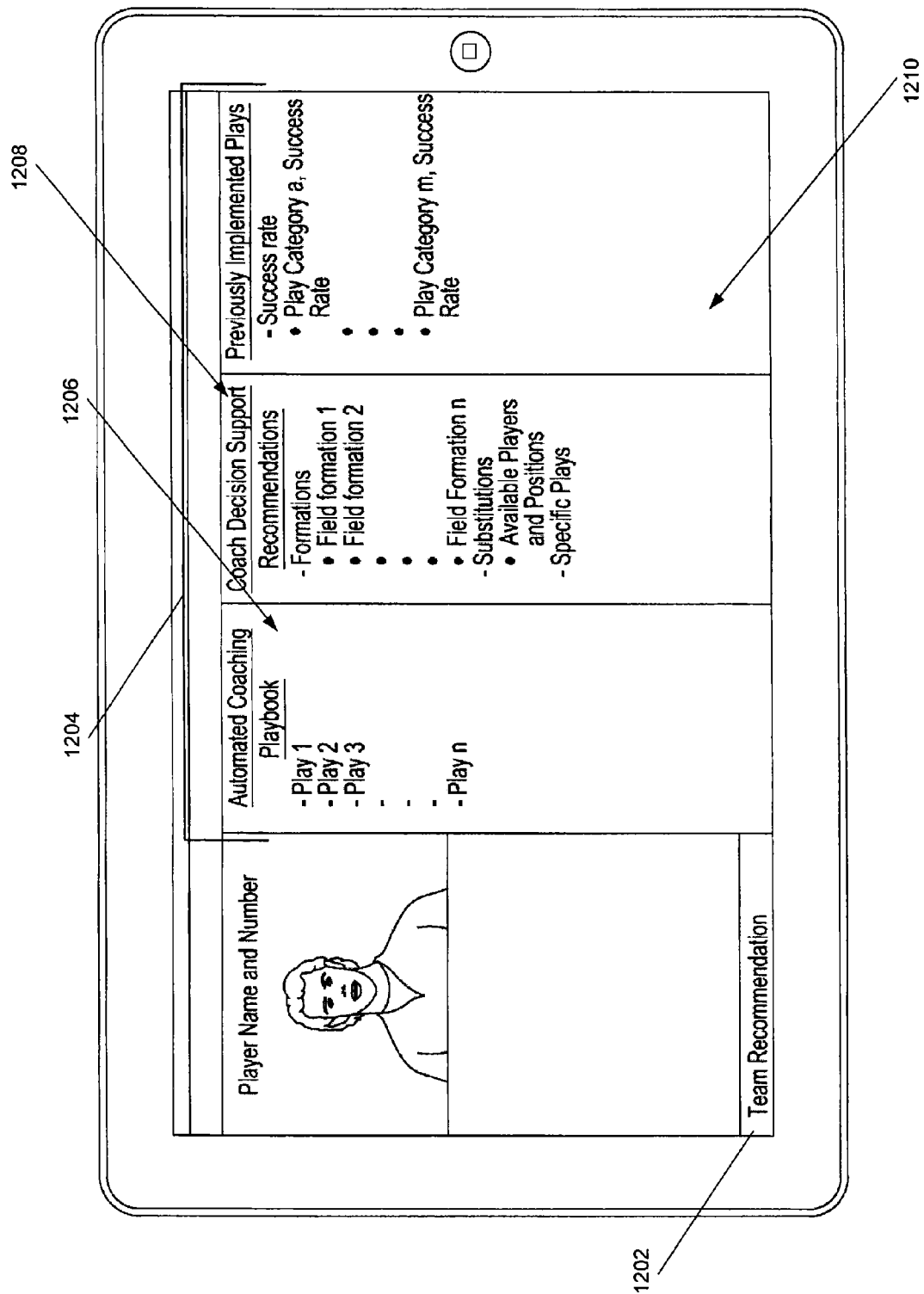
FIG. 12 is an illustration of a coach decision support system user interface displaying an automated coaching playbook, coach decision support recommendations and previously implemented plays according to an embodiment.

FIG. 12 is an illustration of a coach decision support system user interface displaying an automated coaching playbook, coach decision support recommendations and previously implemented plays according to an embodiment. In one example, a coach may select menu item related to viewing team recommendations 1202. In such a case, player/team performance window 1204 may include several sub-windows that illustrate team wide decisions and plays available to the coach. Again, while not shown, the player/team performance window 1204 may further include graphical and statistical data illustrations as previously shown for players, but this time for an entire team.

In one example, player/team performance window 1204 may include automated coaching playbook window 1206. The automated coaching playbook window 1206 may include a list of all of the coach's plays or subsets of the plays, such as defensive and offensive plays and the like. This enables the coach to review his playbook electronically. The player/team performance window 1204 may further include a coach decision support recommendations window 1208. Recommendations window 1208 may list a set of plays or recommendations given the received input data about each individual athlete and collectively for the team of individual athletes. Recommendations may come in form of different formations, substitutions, running specific plays or creating a broader solution based on probabilities. For example, a coach may select field formations at which time a list of field formations will be shown in a drop menu like set up. Next to each formation, the coach decision support system may output an effectiveness score or predicted success rate based on data collected from the field. For example, a formation of 4-3-3 may have an 80% effectiveness rate versus a 4-4-2 which may have 60% effectiveness rate.

In yet another example, if a coach selects specific players ready to be substituted, a drop down menu of available players and positions will be displayed. Furthermore, the coach decision support system may further display player statistics against this particular opponent or season statistics for the player.

Player/team performance window 12-4 may include a previously implemented plays window 1210. This window may illustrate features of previously implemented plays and their success rates. In one embodiment, previously implemented plays window 1210 may demonstrate a list of previously selected plays given the same situation as the coach facing now, for example, down one goal, or energy expenditure of team is high, or whether conditions are of a certain type. For example, the coach decision support system may determine that on a similar match earlier in the season, score, player stats and weather conditions were similar to the conditions of the current game, and as such based on previously recorded data, coach decision support system may output a list of previously utilized plays and their success rates.

Alternatively, previously implemented plays window 1210 may demonstrate the history utilization of each selected play in recommendations window 1208 and associated success rates. This may enable the coach to determine what has previously worked in the past and what has not and why.

FIG. 13 an illustration of a hardware description of a device according to embodiments illustrated in FIGS. 1-12.

Next, a hardware description of a device according to exemplary embodiments illustrated in FIGS. 1-12 is described with reference to FIG. 13. In FIG. 13, the device includes a CPU 1300 which performs the processes described above. The process data and instructions may be stored in memory 1302. These processes and instructions may also be stored on a storage medium disk 1304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the claimed advancements may be provided as a utility application, background daemon, or component of an operating system, or combination thereof, executing in conjunction with CPU 1300 and an operating system such as Microsoft Windows 7, UNIX, Solaris, LINUX, Apple MAC-OS and other systems known to those skilled in the art.

CPU 1300 may be a Xenon or Core processor from Intel of America or an Opteron processor from AMD of America, or may be other processor types that would be recognized by one of ordinary skill in the art. Alternatively, the CPU 1300 may be implemented on an FPGA, ASIC, PLD or using discrete logic circuits, as one of ordinary skill in the art would recognize. Further, CPU 1300 may be implemented as multiple processors cooperatively working in parallel to perform the instructions of the inventive processes described above.

The device in FIG. 13 also includes a network controller 1306, such as an Intel Ethernet PRO network interface card from Intel Corporation of America, for interfacing with network 77. As can be appreciated, the network 77 can be a public network, such as the Internet, or a private network such as an LAN or WAN network, or any combination thereof and can also include PSTN or ISDN sub-networks. The network 77 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The device further includes a display controller 1308, such as a NVIDIA GeForce GTX or Quadro graphics adaptor from NVIDIA Corporation of America for interfacing with display 1310, such as a Hewlett Packard HPL2445w LCD monitor. A general purpose I/O interface 1312 interfaces with a keyboard and/or mouse 1314 as well as a touch screen panel 1316 on or separate from display 1310. General purpose I/O interface also connects to a variety of peripherals 1318 including printers and scanners, such as an OfficeJet or DeskJet from Hewlett Packard.

A sound controller 1320 is also provided in the device, such as Sound Blaster X-Fi Titanium from Creative, to interface with speakers/microphone 1322 thereby providing sounds and/or music.

The general purpose storage controller 1324 connects the storage medium disk 1304 with communication bus 1326, which may be an ISA, EISA, VESA, PCI, or similar, for interconnecting all of the components of the device. A description of the general features and functionality of the display 1310, keyboard and/or mouse 1314, as well as the display controller 1308, storage controller 1324, network controller 1306, sound controller 1320, and general purpose I/O interface 1312 is omitted herein for brevity as these features are known.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A coach decision support method comprising:
    collecting sensor data associated with an athlete at a data logger circuitry, wherein the sensor data is generated by at least one sensor placed on the athlete;
    pre-processing the sensor data at the data logger circuitry by filtering sensor noise from the sensor data;
    extracting at least one feature set from the collected sensor data;
    classifying with the circuitry the at least one extracted feature set into at least one physical activity;
    transmitting the physical activity classification to a data analysis circuitry;
    generating with the data analysis circuitry a report of the physical activity indicative of a performance of the athlete within a sporting venue;
    generating with the data analysis circuitry at least one coach decision recommendation based at least in part on the report;
    generating a coach decision support algorithm to provide intelligent monitoring of the athlete and at least one other athlete within the sporting venue; and
    outputting at least one optimal decision recommendation as a function of generated individual movement patterns, individual energy expenditure patterns, and team movement patterns.

2. The method of claim 1, further comprising:
    collecting global positioning (GPS) data associated with a position of the athlete;
    generating a player localization map; and
    transmitting the player localization map to the data analysis module.

3. The method of claim 1, wherein the extracting further includes:
    extracting a heart rate associated with the athlete; and
    generating an energy expenditure associated with the athlete.

4. The method of claim 3, wherein generating the energy expenditure further includes:
    collecting temperature and humidity data;
    identifying the physical activity for a predetermined time window; and
    calculating with the data analysis circuitry the energy expenditure by the physical activity as a function of the physical activity and the predetermined time window.

5. The method of claim 4, further comprising:
    calculating with the data analysis circuitry a heat index as a function of temperature and humidity;
    modifying the energy expenditure by the heat index; and
    calculating with the data analysis circuitry a total modified energy expenditure of the athlete.

6. The method of claim 1, wherein pre-processing sensor data further includes:
    filtering noise associated with at least one sensor to minimize interference in transmitted data between the at least one sensor and at least one other sensor.

7. The method of claim 1, wherein the extracting at least one feature set further includes:
    determining at least one body part motion associated with the transmitted sensor data.

8. The method of claim 7, wherein the classifying further includes:
    categorizing a combination of the determined at least one body part motion into a classification of movements including any one of standing, walking running, jogging, kicking, dribbling, jumping, or sprinting.

9. The method of claim 1, wherein the detailed report includes:
    individual movement patterns of the athlete in relation to at least one moving object and in further relation to at least one other athlete within the sporting venue.

10. The method of claim 9, wherein individual movement patterns further includes:
    location and time history of the movement patterns according to the athlete's position within the sporting venue; and
    moving object possession patterns.

11. The method of claim 9, further comprising:
    generating team movement patterns to analyze team activities within the sporting venue, wherein the team movement patterns include team coordinated patterns, moving object passing patterns, and attacking and defending patterns.

12. The method of claim 1, wherein the optimal decision recommendation further includes:
    presenting an automated playbook on a user interface, wherein the automated playbook includes at least one play; and
    present a generated play recommendation option on the user interface.

13. The method of claim 12, wherein the generated play recommendation is generated based on:
    the generated detailed report and further based on a pre-installed playbook; and
    a score metric associated with highest probability of success of the play based on the detailed report statistics.

14. The method of claim 1, wherein the optimal decision recommendation further includes:
    presenting a player substitution metric on a user interface, wherein the athlete substitution metric is based at least in part on the athlete data in the detailed report.

15. The method of claim 1, wherein the optimal decision recommendation further includes:
    generating coaching advice and player motivational tactics on a user interface based on the generated detailed report.

16. The method of claim 1, wherein the optimal decision recommendation further includes:
    generating a game analysis report based on the generated detailed report, wherein the game analysis report further includes performance data associated with at least one athlete, a group of athletes, or an entire team; and
    generating a training recommendation report based at least in part on the generated detailed report.

17. A coach decision support system comprising:
at least one data generating sensor configured to generate data associated with at least one athlete and further configured to be placed on the at least one athlete; and
electronic circuitry configured to
- collect sensor data from the at least one data generating sensor,
- pre-process the sensor data to filter sensor noise from the data,
- extract at least one feature of the collected sensor data,
- classify the at least one extracted feature into at least one physical activity,
- transmit the physical activity classification to a data analysis circuitry,
- generate a report of the physical activity classification indicative of a performance of the athlete within a sporting venue,
- generate at least one coach decision recommendation based at least in part on the report,
- generate a coach decision support algorithm to provide intelligent monitoring of the at least one athlete and at least one other athlete within the sporting venue, and
- output at least one optimal decision recommendation as a function of generated individual movement patterns, individual energy expenditure patterns, and team movement patterns.

18. The coach decision support system of claim 17, further comprising:
a user-interface module configured to present at least one of an automated playbook and play recommendation, a player substitution recommendation, a coaching advice recommendation, and a game analysis and training recommendation.

19. A non-transitory computer readable storage medium having computer readable instructions that when executed by a processing circuit implement a method of a coach decision support, the method comprising:
- collecting sensor data associated with an athlete at a data logger circuitry, wherein the sensor data is generated by at least one sensor placed on the athlete;
- pre-processing the sensor data at the data logger circuitry by filtering sensor noise from the sensor data;
- extracting at least one feature set from the collected sensor data;
- classifying, with processing circuitry, the at least one extracted feature set into at least one physical activity;
- transmitting the physical activity classification to a data analysis circuitry;
- generating, with the data analysis circuitry, a report of the physical activity indicative of a performance of the athlete within a sporting venue;
- generating, with the data analysis circuitry, at least one coach decision recommendation based at least in part on the report;
- generating, with the data analysis circuitry, a coach decision support algorithm to provide intelligent monitoring of the athlete and at least one other athlete within the sporting venue; and
- outputting, with the data analysis circuitry, at least one optimal decision recommendation as a function of generated individual movement patterns, individual energy expenditure patterns, and team movement patterns.

* * * * *